(12) United States Patent
Armstrong

(10) Patent No.: US 7,643,881 B2
(45) Date of Patent: Jan. 5, 2010

(54) NEUROSTIMULATION WITH ACTIVATION BASED ON CHANGES IN BODY TEMPERATURE

(75) Inventor: Randolph K. Armstrong, Houston, TX (US)

(73) Assignee: Cyberonics, Inc., Houston, TX (US)

( * ) Notice: Subject to any disclaimer, the term of this patent is extended or adjusted under 35 U.S.C. 154(b) by 672 days.

(21) Appl. No.: 11/336,453

(22) Filed: Jan. 20, 2006

(65) Prior Publication Data

US 2006/0142802 A1 Jun. 29, 2006

Related U.S. Application Data

(63) Continuation-in-part of application No. 11/009,122, filed on Dec. 10, 2004, now Pat. No. 7,366,571.

(51) Int. Cl.
*A61B 5/01* (2006.01)
*A61N 1/36* (2006.01)
(52) U.S. Cl. ........................................ 607/45; 600/549
(58) Field of Classification Search ................. 607/1–3, 607/45, 48, 105, 113, 116; 600/300–301, 600/544–545, 549
See application file for complete search history.

(56) References Cited

U.S. PATENT DOCUMENTS

| | | | |
|---|---|---|---|
| 3,796,221 A | | 3/1974 | Hagfors |
| 4,297,685 A | * | 10/1981 | Brainard, II ................. 340/575 |
| 4,612,934 A | | 9/1986 | Borkan |
| 4,702,254 A | | 10/1987 | Zabara |
| 4,782,836 A | * | 11/1988 | Alt ............................... 607/19 |
| 4,793,353 A | | 12/1988 | Borkan |
| 4,867,164 A | | 9/1989 | Zabara |

(Continued)

FOREIGN PATENT DOCUMENTS

WO WO 2004363772 A2 4/2004

(Continued)

OTHER PUBLICATIONS

Bachman, D.S, et al., "Effects of Vagal Volleys and Serotonin on Units of Cingulate Cortex in Monkeys," Brain Research, 130, (1977), pp. 253-269.

(Continued)

*Primary Examiner*—Carl H Layno
*Assistant Examiner*—Jessica Reidel
(74) *Attorney, Agent, or Firm*—Conley Rose, P.C.; Timothy L. Scott, Esq.

(57) ABSTRACT

Methods and devices for detecting and/or predicting onset of an undesirable physiological event or neural state, such as an epileptic seizure, facilitate rapid intervention with a treatment therapy such as neurostimulation or drug therapy. The methods and devices involve monitoring the patient's body temperature, preferably by an implanted temperature sensor, to detect a change in a body temperature parameter over a first time period, which may comprise an increase or decrease in the patient's body temperature, time rate of change of body temperature, moving average temperature, increase or decrease in body temperature exceeding a target temperature, elevated or reduced body temperature, or temperature stability parameter over a first time period. The sampling period may be changed manually or depending upon a sensed body parameter, including temperature. When a parameter change is detected that exceeds a threshold, neurostimulation therapy is delivered to a neural structure of the patient.

15 Claims, 5 Drawing Sheets

U.S. PATENT DOCUMENTS

| | | | |
|---|---|---|---|
| 4,873,655 A | | 10/1989 | Kondraske |
| 4,905,697 A | * | 3/1990 | Heggs et al. .................. 607/18 |
| 5,025,807 A | | 6/1991 | Zabara |
| 5,089,019 A | * | 2/1992 | Grandjean ................ 623/3.12 |
| 5,111,815 A | | 5/1992 | Mower |
| 5,188,104 A | | 2/1993 | Wernicke et al. |
| 5,199,428 A | | 4/1993 | Obel et al. |
| 5,203,326 A | | 4/1993 | Collins |
| 5,205,285 A | | 4/1993 | Baker, Jr. |
| 5,311,876 A | | 5/1994 | Olsen et al. |
| 5,330,507 A | | 7/1994 | Schwartz |
| 5,336,244 A | * | 8/1994 | Weijand ..................... 607/21 |
| 5,540,734 A | | 7/1996 | Zabara |
| 5,611,350 A | | 3/1997 | John |
| 5,645,570 A | | 7/1997 | Corbucci |
| 5,658,318 A | | 8/1997 | Stroetmann et al. |
| 5,683,422 A | | 11/1997 | Rise et al. |
| 5,690,681 A | | 11/1997 | Geddes et al. |
| 5,700,282 A | | 12/1997 | Zabara |
| 5,702,429 A | | 12/1997 | King |
| 5,755,750 A | | 5/1998 | Petruska et al. |
| 5,792,186 A | | 8/1998 | Rise |
| 5,814,087 A | * | 9/1998 | Renirie ..................... 607/21 |
| 5,814,092 A | | 9/1998 | King |
| 5,833,709 A | | 11/1998 | Rise et al. |
| 5,861,014 A | | 1/1999 | Familoni |
| 5,913,882 A | | 6/1999 | King |
| 5,916,239 A | | 6/1999 | Geddes et al. |
| 5,928,272 A | | 7/1999 | Adkins et al. |
| 5,978,702 A | | 11/1999 | Ward et al. |
| 5,987,352 A | | 11/1999 | Klein et al. |
| 5,995,868 A | | 11/1999 | Osorio et al. |
| 6,016,449 A | | 1/2000 | Fischell et al. |
| 6,018,682 A | | 1/2000 | Rise |
| 6,044,846 A | | 4/2000 | Edwards |
| 6,061,593 A | | 5/2000 | Fischell et al. |
| 6,092,528 A | | 7/2000 | Edwards |
| 6,128,538 A | | 10/2000 | Fischell et al. |
| 6,134,474 A | | 10/2000 | Fischell et al. |
| 6,141,590 A | | 10/2000 | Renirie et al. |
| 6,208,894 B1 | | 3/2001 | Schulman et al. |
| 6,253,109 B1 | | 6/2001 | Gielen |
| 6,266,564 B1 | | 7/2001 | Hill et al. |
| 6,304,775 B1 | | 10/2001 | Iasemidis et al. |
| 6,319,241 B1 | | 11/2001 | King et al. |
| 6,327,503 B1 | | 12/2001 | Familoni |
| 6,337,997 B1 | | 1/2002 | Rise |
| 6,341,236 B1 | | 1/2002 | Osorio et al. |
| 6,360,122 B1 | | 3/2002 | Fischell et al. |
| 6,366,813 B1 | | 4/2002 | DiLorenzo |
| 6,459,936 B2 | | 10/2002 | Fischell et al. |
| 6,466,822 B1 | | 10/2002 | Pless |
| 6,473,639 B1 | | 10/2002 | Fischell et al. |
| 6,477,417 B1 | | 11/2002 | Levine |
| 6,477,418 B2 | | 11/2002 | Plicchi et al. |
| 6,480,743 B1 | | 11/2002 | Kirkpatrick et al. |
| 6,522,928 B2 | | 2/2003 | Whitehurst et al. |
| 6,542,774 B2 | | 4/2003 | Hill et al. |
| 6,549,804 B1 | | 4/2003 | Osorio et al. |
| 6,567,703 B1 | | 5/2003 | Thompson et al. |
| 6,587,726 B2 | | 7/2003 | Lurie et al. |
| 6,594,524 B2 | | 7/2003 | Esteller et al. |
| 6,647,296 B2 | | 11/2003 | Fischell et al. |
| 6,662,048 B2 | * | 12/2003 | Balczewski et al. ........... 607/21 |
| 6,671,555 B2 | | 12/2003 | Gielen et al. |
| 6,671,556 B2 | | 12/2003 | Osorio et al. |
| 6,768,969 B1 | | 7/2004 | Nikitin et al. |
| 6,920,357 B2 | | 7/2005 | Osorio et al. |
| 6,944,501 B1 | | 9/2005 | Pless |
| 6,961,618 B2 | | 11/2005 | Osorio et al. |
| 7,006,872 B2 | | 2/2006 | Gielen et al. |
| 7,050,856 B2 | | 5/2006 | Sypullkowski |
| 7,204,833 B1 | * | 4/2007 | Osorio et al. ................. 606/22 |
| 7,366,571 B2 | * | 4/2008 | Armstrong ................... 607/45 |
| 2002/0151939 A1 | | 10/2002 | Rezai |
| 2003/0181954 A1 | | 9/2003 | Rezai |
| 2003/0195588 A1 | * | 10/2003 | Fischell et al. ................. 607/55 |
| 2004/0015205 A1 | | 1/2004 | Whitehurst et al. |
| 2004/0082984 A1 | * | 4/2004 | Osorio et al. ............... 607/105 |
| 2004/0172091 A1 | | 9/2004 | Rezai |
| 2005/0021092 A1 | | 1/2005 | Yun et al. |
| 2005/0021103 A1 | | 1/2005 | DiLorenzo |
| 2005/0021104 A1 | | 1/2005 | DiLorenzo |
| 2005/0060010 A1 | | 3/2005 | Goetz |
| 2005/0065562 A1 | | 3/2005 | Rezai |
| 2005/0065573 A1 | | 3/2005 | Rezai |
| 2005/0119703 A1 | | 6/2005 | DiLorenzo |
| 2006/0095081 A1 | | 5/2006 | Zhou et al. |

FOREIGN PATENT DOCUMENTS

WO     WO 2005028026 A1     3/2005

OTHER PUBLICATIONS

Bohning, D.E. et al., "Feasibility Of Vagus Nerve Stimulation-Synchronized Blood Oxygenation Level-Dependent Functional MRI," Investigative Radiology, vol. 36, No. 8, (Aug. 2001), pp. 470-479.

Clark, K.B., et al., "Posttraining Electrical Stimulation Of Vagal Afferents With Concomitant Vagal Efferent Inactivation Enhances Memory Storage Processes In The Rat," Neurobiology Of Learning And Memory 70, Article No. NL983863, (1998) pp. 364-373.

Hallowitz, R.A., et al., "Effects of Vagal Volleys on Units of Intralaminar and Juxtalaminar Thalamic Nuclei in Monkeys," Brain Research, 130, (1977), pp. 271-286.

Koo, Betty, "EEG Changes With Vagus Nerve Stimulation," Journal Of Clinical Neurophysiology, vol. 18, No. 5, (Sep. 2001), pp. 434-441.

Lockard, J.S., et al., "Feasibility and Safety of Vagal Stimulation in Monkey Model," Epilepsia, 31, (Suppl.2), (1990), pp. S20-S26.

Terry, R.S., et al., "The Implantable Neurocybernetic Prosthesis System," Pacing and Clinical Electrophysiology, vol. 14, No. 1, (Jan. 1991), pp. 86-93.

Vonck, K., et al., "The Mechanism of Action of Vagus Nerve Stimulation for Refractory Epilepsy," Journal of Neurophysiology, vol. 18, No. 5, (Sep. 2001), pp. 394-401.

Woodbury, J.W., et al., "Vagal Stimulation Reduces the Severity of Maximal Electroshock Seizures in Intact Rats: Use of Cuff Electrode for Stimulating and Recording," PACE, vol. 14, (Jan. 1991), pp. 94-107.

Zabara, J., "Inhibition of Experimental Seizures in Canines by Repetitive Vagal Stimulation," Epilepsia, 33(6), (1992), pp. 1005-1012.

\* cited by examiner

NEUROSTIMULATION WITH ACTIVATION BASED ON CHANGES IN BODY TEMPERATURE

CROSS-REFERENCE TO RELATED APPLICATION

This application is a continuation-in-part of U.S. Ser. No. 11/009,122, now U.S. Pat. No. 7,366,571, "Neurostimulator With Activation Based On Changes In Body Temperature," filed Dec. 10, 2004 in the name of Randolph K. Armstrong.

BACKGROUND OF THE INVENTION

1. Field of the Invention

This invention relates generally to implantable medical devices, and more particularly to medical devices that may be activated or adapted to one or more physiological conditions in a patient in which the devices are implanted.

2. Background

There have been many improvements over the last several decades in medical treatments for disorders of the nervous system, including epilepsy and other motor disorders, and conditions caused by or involving abnormal neural discharge. One of the more recently available treatments involves applying an electrical signal to reduce symptoms or effects of such neural disorders. For example, electrical signals have been successfully applied to neural tissue in the human body to provide various benefits, including reducing occurrences of seizures and/or improving or ameliorating other conditions such as depression. A particular example of such a treatment regimen involves applying an electrical signal to the vagus nerve of the human body to reduce or eliminate epileptic seizures, as described in U.S. Pat. No. 4,702,254 to Dr. Jacob Zabara, which is hereby incorporated by reference in its entirety in this specification.

Electrical stimulation of the vagus nerve may be provided by implanting an electrical device underneath the skin of a patient, detecting a precursor, symptom or effect associated with the condition, and delivering electrical stimulation pulses to the vagus nerve. Alternatively, the system may operate without a detection system if the patient has been diagnosed with epilepsy, and the device may simply apply a series of electrical pulses to the vagus nerve (or another cranial nerve) intermittently throughout the day, or over another predetermined time interval. Stimulation that involves a detection and/or sensing operation is referred to as active stimulation, while stimulation without a detection or sensing operation is known as passive stimulation.

Many implantable pulse generators used for electrical stimulation of neurological tissue operate according to a therapy algorithm programmed into the device by a health care provider such as a physician. One or more parameters of the therapy (e.g., current amplitude, pulse width, pulse frequency, and on-time and off-time) may thereafter be changed by reprogramming the neurostimulator after implantation by transcutaneous communication between an external programming device and the implanted neurostimulator. The ability to program (and later re-program) the implanted device permits a health care provider to customize the stimulation therapy to the patient's needs, and to update the therapy periodically should those needs change.

It is desirable, however, for an implantable medical device, such as a neurostimulator, to be able to provide active stimulation by automatically detecting one or more physiological parameters and responsively initiating a stimulation therapy specifically tailored to the physiological parameters detected, without the necessity of intervention by a health care provider. The detected parameters preferably indicate the onset or potential onset of an undesirable physiological event, such as an epileptic seizure. Detection of such physiological events is, however, complicated by physiological differences among patients.

SUMMARY OF THE INVENTION

In one aspect, the present invention provides improved methods of detecting and/or predicting the onset of an undesirable physiological event or neural state, such as an epileptic seizure, in order to facilitate rapid intervention with a treatment therapy such as neurostimulation or drug therapy. In many instances, a rapid rise or fall in temperature or a prolonged period at an elevated temperature (e.g., fever) or reduced temperature (e.g., hypothermia) may increase the likelihood of epileptic and febrile seizures. Alternatively, the temperature of a patient undergoing a physiological event such as an epileptic seizure may undergo a sudden, rapid fluctuation up or down shortly before or contemporaneous with seizure onset. In one embodiment, the invention comprises monitoring the patient's body temperature, preferably by an implanted temperature sensor, to detect a body temperature parameter that is not indicative of physical exercise or normal physiological conditions unrelated to the undesirable physiological event. The temperature parameter may comprise an increase or decrease in the patient's body temperature exceeding a predetermined magnitude, a time rate of change of body temperature exceeding a threshold level, a difference in a moving average temperature for a first period from that of a second period, a predetermined duration at an elevated or reduced body temperature, and/or a stability or instability of temperature over time. By way of nonlimiting example, the temperature parameter may comprise a body temperature rise (or fall) of a first magnitude, or a body temperature rise (or fall) of a predetermined magnitude within a predetermined time period (i.e., a threshold time rate of change up or down), or an elevated (or reduced) body temperature of a predetermined magnitude for a predetermined time period.

The invention also provides methods of providing electrical neurostimulation therapy to treat an undesirable physiological event or neural state by responding to a detected temperature parameter change by initiating or altering a therapy regimen. In a preferred embodiment the responsive treatment comprises a neurostimulation therapy, more preferably electrical stimulation of a cranial nerve, and most preferably electrical stimulation of the vagus nerve. In one embodiment, the responsive treatment comprises initiating vagus nerve stimulation (VNS) according to programmed stimulation parameters. In an alternative embodiment, the responsive treatment comprises changing one or more parameters of an existing VNS regimen already implemented. The responsive treatment may, in a different embodiment, comprise initiating electrical stimulation to a trigeminal and/or a glossopharyngeal nerve of the patient rather than (or in addition to) the vagus nerve. In a still further embodiment, the responsive treatment comprises providing a drug therapy from a drug pump coupled to the patient's body.

To provide a more efficacious temperature detection algorithm for the patient that reduces the likelihood of a false positive indication, the patient may be tested by one or more exercise, physiological or environmental tests to determine a maximum rate of temperature change associated with exercise or other physiological conditions (e.g., a rapid change in environmental temperature such as emerging from a temperature-controlled building into extremely hot or cold outside conditions, natural circadian temperature variations, water activities such as immersion in extremely cold water, thermal springs or hot tubs, and saunas.). The maximum (and/or minimum) body temperature, rate of temperature changes, moving average temperatures, duration at high/low temperature, stability or instability of temperature, and/or other body temperature parameters occurring during the tests may be recorded or determined and used in methods and devices of the present invention to ensure that the body temperature parameter detected and used to trigger neurostimulation is beyond a threshold value, which may correspond to normal physiological changes for the patient. There may also be situations when the body temperature parameter may increase the likelihood of seizures in certain patients, despite being within a range that may be physiologically normal. In these situations, the present invention may be used to trigger neurostimulation despite some possibility that the body temperature parameter may be asymptomatic.

The precise mechanism for the temperature fluctuations that are a precursor of an epileptic seizure is not fully understood at present. Without being bound by theory, it is believed that such changes may arise from instability of autonomic tone caused by electrical activity associated with a seizure. There is, however, uncertainty as to the relative contributions of the sympathetic and parasympathetic nervous system influences on autonomic tone. It is also possible that an instability of autonomic tone and temperature instability precede changes in the patient's electroencephalogram (EEG) readings or other physical manifestations of seizure activity, such as uncontrollable violent movements. In any case, if the responsive treatment can be implemented sooner, there will be a greater likelihood that the seizure (or other undesired physiological event or neural state) can be inhibited altogether, terminated sooner, or reduced in either severity or duration.

In another aspect, the present invention provides a neurostimulator system comprising a pulse generator capable of generating an electrical pulse to stimulate a neural structure (such as a cranial nerve) in a patient, a stimulation electrode assembly, and at least one temperature sensor element. The temperature sensor element may be considered as part of a temperature sensing unit that is, in turn, part of a controller for regulating how the neurostimulation therapy is applied to the neural structure.

The temperature sensing unit measures and analyzes body temperature to derive temperature parameters that may be used to initiate or alter a neurostimulation therapy when a temperature parameter exceeds a threshold value. The temperature parameters may include body temperature, rate of change of body temperature, differences in moving average body temperatures over different time domains or intervals, prolonged periods at elevated or reduced temperatures, or stability and/or instability of temperature (which may defined as variation and/or lack of variation of temperature over time, measured using standard deviation, range, or other measure of variation). In addition to the temperature sensing element, the temperature sensing unit preferably comprises timing circuitry for controlling the sampling rate at which temperature is sensed with the sensor element, temperature analysis circuitry for calculating temperature parameters and/or analyzing a temperature data stream from the temperature sensor element(s), and activation circuitry for initiating or altering a neurostimulation therapy. The controller is also preferably comprises a memory element for storing temperature data from the temperature sensing unit.

The temperature sensor element may comprise any of a number of different types of sensors, so long as it is capable of sensing temperature when implanted in the body of the patient. In one embodiment the sensor element comprises a silicon-based temperature sensor integrated into a microprocessor or other integrated circuit. In another embodiment, the temperature sensor may comprise an electrode or thermocouple coupled to the distal end of a lead whose proximal end is coupled to the pulse generator. In any event, the temperature sensor element is coupled to the pulse generator and senses a body temperature of the patient.

In preferred embodiments, the pulse generator comprises a biocompatible case enclosing and protecting a battery and the internal pulse generation circuitry such as the controller. In preferred embodiments, the pulse generator, stimulation electrode assembly, and controller (including the temperature sensing unit) are all implantable. In alternative embodiments, one or more of the components of the system may be external.

In a particular embodiment of the neurostimulation system, a temperature sensor provides a time series data stream of body temperature measurements for the patient, which is stored in a memory. The controller may be programmed to sample the temperature at a desired interval ranging from 0.01 seconds to 24 hours or more. In preferred embodiments, the temperature is measured at intervals from 1 second to 6 hours, and more preferably from 5 minutes to 4 hours. Because of memory or power limitations associated with continuous temperature measurements in an implantable medical device, in certain embodiments of the invention the controller may be programmed to change the sampling interval based upon detected conditions. In one embodiment, the controller may be programmed to change the sampling interval from a longer interval to a shorter interval when a specified body temperature parameter is detected, e.g., a predetermined rate of change of body temperature or a predetermined elevated or reduced temperature (fever or hypothermia). The controller may also change the sampling interval from a shorter interval to a longer interval when another specified body temperature parameter is detected. Changing the body temperature sampling rate based on the patient's condition may be used to significantly reduce the power burden of certain embodiments of the invention.

Temperature analysis circuitry analyzes the temperature data stream to measure or calculate and store various temperature parameters, including body temperature, running averages of body temperature, and rates of change of body temperature over several time period domains that may range from one second to 24 hours or more. These time domains may comprise, without limitation, 1 second, 10 seconds, 15 seconds, 30 seconds, 1 minute, 2 minutes, 5 minutes, 10 minutes, 15 minutes, 30 minutes, 1 hour, 2 hours, 3 hours, 4 hours, 6 hours, 12 hours and 24 hours.

In one embodiment, the temperature analysis circuitry determines and maintains a log of the minimum and maximum temperatures, running average temperatures, and rates of change of temperature over one or more time domains. Because individual temperature measurements may be highly variable, calculations of time rate of change of temperature may be based on moving averages rather than individual temperature readings. For example, a time rate of change for a 1 minute temperature domain may be calculated as temperature change per minute by comparing a moving average for a five second period with the five second moving average for the time period exactly one minute prior to the first moving average. Similarly, a five minute time rate of change may be calculated as temperature change per minute by subtracting a moving average of a 1 second domain from a second 1 second moving average for a period exactly five minutes later and dividing the difference by five. Alternatively, individual temperature readings instead of moving averages may be used to calculate time rates of temperature change.

The temperature analysis circuitry may also calculate and compare shorter term running average temperatures (e.g., 10 seconds, 30 seconds) to longer term running averages (e.g., 10 minutes, 30 minutes, 1 hour). For example, a short term running average temperature for the previous 1 minute time domain may be continuously compared with a longer term running average for the past 10 minutes, and the difference may be stored.

The temperature analysis circuitry may also be used to determine a time period during which body temperature has been elevated above a predetermined temperature threshold or reduced below a different threshold. The thresholds may be programmable.

In another embodiment, the temperature analysis circuitry may also determine the stability (or instability) of temperature by calculating one or more parameters indicative of the variability of body temperature measurements over a predetermined period of time. This may include calculating the difference between minimum and maximum temperatures for the period (i.e., the range), the standard deviation among the measurements taken during the period, the difference between the minimum and maximum rate of change, the standard deviation of the rate of change and other statistical parameters that may be used as a measure of temperature stability.

One or more of temperature, time rate of change of temperature, changes in moving averages of temperature, duration at an elevated or reduced temperature, and/or stability or instability of temperature may be compared to an appropriate threshold for the particular parameter(s) to provide an indication of the occurrence of an undesirable physiological event or neural state, such as onset, impending onset, or increased probability of an epileptic seizure. The programmed threshold for temperature may be set at a temperature above normal body temperature or a higher temperature above a body temperature associated with exercise. In another embodiment, a temperature drop of even slightly below normal or circadian body temperature may be taken to indicate an undesirable medical condition. The threshold for time rate of change of temperature is preferably set at a rate that exceeds the rate of temperature change during periods of intense exercise. A negative threshold may also be set at a temperature drop exceeding that of moving from a warm environment to an extremely cold environment.

Changes in moving average temperatures may be compared to screen out changes associated with exercise periods and moving from a warm to a cold environment or vice versa. These thresholds may be set at a slope or grade representative of, for example, an increase or decrease in absolute temperature exceeding 1° F. within 3 minutes or less. The foregoing examples are provided as nonlimiting examples only. Thresholds may be used individually or in combination to reduce detection of non-physiologic changes that are not associated with an epileptic seizure or other undesired neural condition. In a preferred embodiment, the patient may be tested by monitoring body temperature after the device is implanted during several periods of exercise for short periods of time. In this manner maximum temperature parameters for normal physiological conditions may be easily determined and the thresholds programmed on an individual basis.

Once temperature parameter thresholds are established, parameters exceeding these thresholds may be detected by the temperature analysis circuit and the temperature sensor.

The temperature analysis circuitry preferably generates a therapy initiation signal and sends the signal to the activation circuitry for initiating or altering a neurostimulation therapy. In one embodiment, the signal simply causes the activation circuitry to activate the neurostimulation therapy according to the existing programming for either the automatic periodic or manually initiated therapy. In another embodiment, the activation circuitry alters the therapy by increasing or decreasing one or more stimulation parameters for a predefined period of time, such as changing the duty cycle by increasing the stimulation on-time from 30 seconds to stimulation 60 seconds for a period of thirty minutes, or decreasing the off-time from 5 minutes to 1 minute. At the conclusion of the predetermined time period, the original parameter settings may be restored. In a different embodiment, the activation circuitry alters the therapy by increasing the stimulation current by 0.5 milliamps for a similar time period before returning to the prior setting. As with all therapies, stimulation parameter safeguards (i.e., maximum and/or minimum allowable settings) are preferably used to ensure safety. It is believed that such a therapy initiation circuit, when implemented in a vagus nerve stimulator system, may inhibit, abort, or alleviate an epileptic seizure or other undesired physiological event.

Cranial nerve stimulation therapy is not harmful to the patient even if the therapy initiation signal arises from a false positive indication of the presence of an undesirable medical condition. Accordingly, the device may also be programmed to initiate or alter neurostimulation therapy whenever one or more temperature parameters exceeds a threshold that may be consistent with an undesirable medical condition, without regard to whether or not the change may also be consistent with normal physiological activity. In this instance, temperature parameter thresholds may be established by a training protocol designed to determine temperature parameter fluctuations that may indicate an undesirable medical condition. The implantable neurostimulator may provide such a trained response by implementing a method that comprises sensing temperature with the temperature sensor, generating a time series of signals representative of the body temperature of the patient, and storing the time series temperature data stream in a memory. The method further comprises determining when an undesired physiological event has occurred in a patient, and providing an indication of the occurrence of the event to the controller. In response to the indication of the physiological event, the temperature analysis circuitry analyzes the stored time series temperature data stream for a predetermined time interval preceding (and possibly after) the event to determine temperature extrema, rates of temperature change, differences in time weighted moving averages within that period, duration at an elevated or reduced temperature, and/or stability or instability of temperature over time as one or more temperature parameter markers to predict the undesired physiological event (e.g., an epileptic seizure). The method also comprises continuing to monitor the temperature data stream for the presence of the marker(s) and, if one or more marker is present in the continuing data stream, initiating or altering the neurostimulation.

In another embodiment, the invention comprises a method of detecting and providing therapy for an undesired physiological event such as an epileptic seizure. The method comprises using a temperature sensing element to generate a time series of patient body temperature measurements, analyzing the time series of patient body temperature measurements to determine at least one temperature parameter, and delivering electrical stimulation pulses to a cranial nerve when a change in the at least one temperature parameter exceeds a predetermined threshold change value. The time series of body temperature measurements may be stored in a memory element to facilitate the analysis of the data. The temperature parameter change may comprise an increase or decrease in the patient's body temperature, a time rate of change of body temperature over a first time domain, or a difference in a moving average temperature for a first period from that of a second period. The sensing element may comprise a temperature sensor incorporated into a microprocessor. The threshold value may comprise a value associated with the undesired physiological event.

In another embodiment, the invention comprises a method of detecting and providing therapy for an undesired physiological event indicated by a temperature marker. The method comprises sensing body temperature of a patient in a first temperature sensing step, generating a first time series temperature data stream for the patient, and storing the data stream in a memory. The method further comprises determining when an undesired physiological event has occurred, providing an indication of the occurrence of the undesired physiological event, and analyzing the time series temperature data stream for a predetermined time interval preceding said event to determine at least one temperature marker in the data stream associated with the event. Following determination of the temperature marker, the method comprises sensing body temperature of a patient in a second sensing step, generating a second time series temperature data stream for the patient, optionally storing the second time series data stream in a memory, and analyzing the second time series temperature data stream for the presence of the temperature marker. Finally, the method comprises initiating or altering a neurostimulation therapy in response to the detection of the temperature marker in the second time series data stream.

In another embodiment, the use of extra-physiologic changes in temperature parameters to detect an undesired physiological event may be augmented by one or more sensors for a different physiological parameter that is likewise subject to rapid fluctuation preceding or coincident with the occurrence of the undesired physiological event. In this embodiment, the invention provides an implantable neurostimulator comprising a pulse generator, a stimulation electrode assembly, a plurality of sensors coupled to the pulse generator, and a controller. The plurality of sensors are capable of sensing at least two physiological parameters selected from the group consisting of a temperature parameter, an action potential in a nerve tissue, a heart parameter, a blood parameter, and brain wave activity. In a preferred embodiment, at least one of the plurality of sensors comprises a temperature sensor for sensing body temperature of the patient and generating a time series of temperature data. The controller receives and analyzes the sensor signals from the plurality of sensors; and the pulse generator initiates or changes a neurostimulation therapy regimen in response to the controller's analysis.

The device may additionally be programmed to apply a periodic prophylactic stimulation of the nerve or nerve bundle to modulate its electrical activity in an appropriate manner for inhibiting seizures regardless of whether or not an excessive temperature change is detected.

Accordingly, it is a more specific aim of the present invention to provide methods and apparatus for automatically and selectively modulating the electrical activity of a cranial nerve, preferably the vagus nerve, in a predetermined manner in response to detection of a sudden change in a temperature parameter of the patient's body, to inhibit, abort or alleviate an undesirable physiological event. Detection of such a change of a temperature parameter offers relative ease of detection, reliability as an indicator, and simplicity of the sensor and implant procedure.

BRIEF DESCRIPTION OF THE DRAWINGS

The invention may be understood by reference to the following description taken in conjunction with the accompanying drawings, in which like reference numerals identify like elements, and in which.

Figure 1:
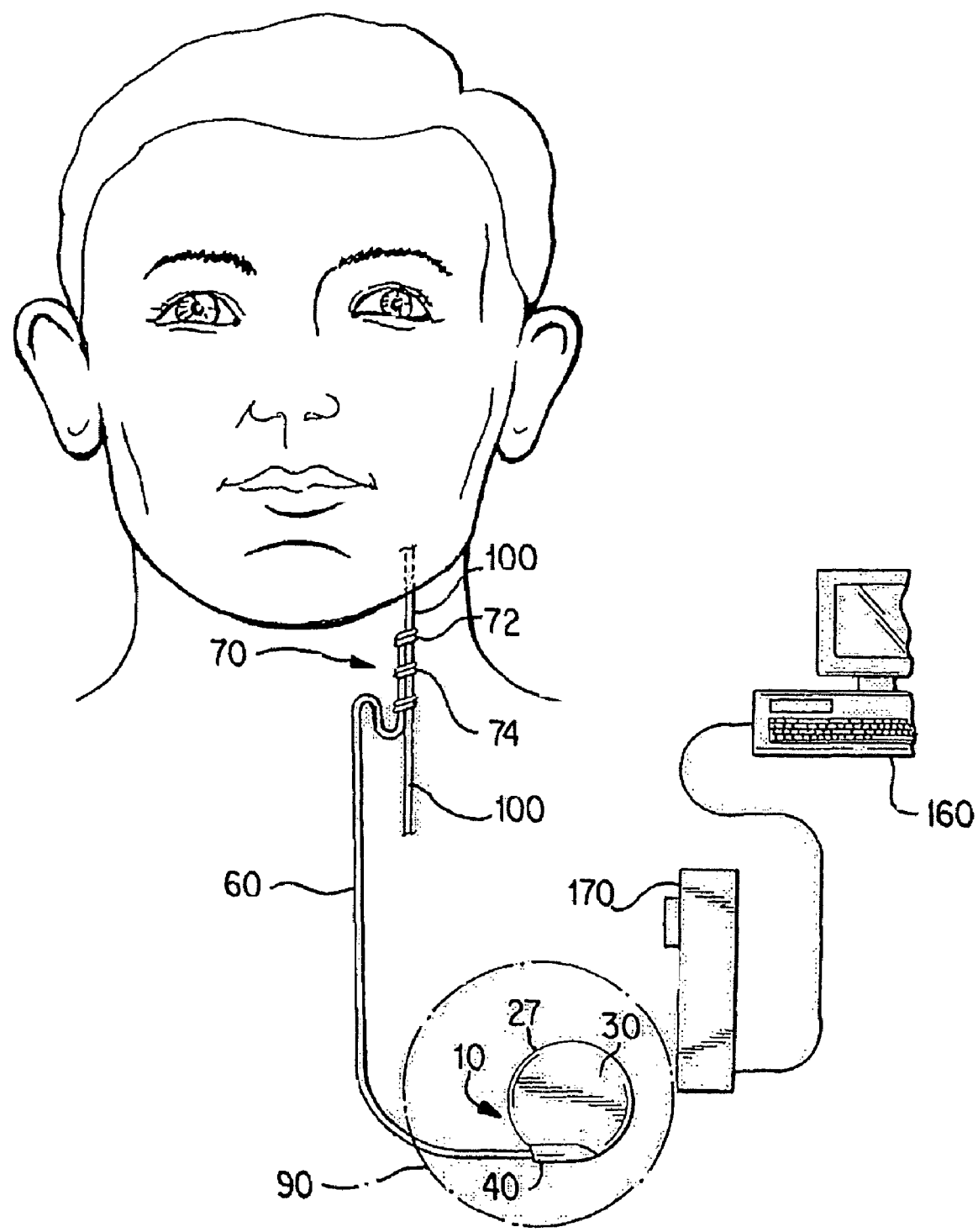
FIG. 1 is a stylized diagram of a prior art implantable medical device suitable for use in stimulating a vagus nerve of a patient, depicted as implanted into a patient's body and showing an external programming system.

While the invention is susceptible to various modifications and alternative forms, specific embodiments thereof have been shown by way of example in the drawings and are herein described in detail. It should be understood, however, that the description herein of specific embodiments is not intended to limit the invention to the particular forms disclosed, but on the contrary, the intention is to cover all modifications, equivalents, and alternatives falling within the spirit and scope of the invention as defined by the appended claims.

DETAILED DESCRIPTION OF SPECIFIC EMBODIMENTS

Illustrative embodiments of the invention are described herein. In the interest of clarity, not all features of an actual implementation are described in this specification. In the development of any such actual embodiment, numerous implementation-specific decisions must be made to achieve the design-specific goals, which will vary from one implementation to another. It will be appreciated that such a development effort, while possibly complex and time-consuming, would nevertheless be a routine undertaking for persons of ordinary skill in the art having the benefit of this disclosure.

The particular embodiments disclosed above are illustrative only, as the invention may be modified and practiced in different but equivalent manners apparent to those skilled in the art having the benefit of the teachings herein. Furthermore, no limitations are intended to the details of construction or design herein shown, other than as described in the claims below. The particular embodiments disclosed above may be altered or modified and all such variations are considered within the scope and spirit of the invention. Accordingly, the protection sought herein is as set forth in the claims below.

FIG. 1 illustrates a prior art neurostimulation system for stimulation of the vagus nerve 100 of a patient. Pulse generator 10 is provided with a main body 30 comprising a case or shell 27 (FIG. 1) with a header 40 having one or more connectors 50 (FIG. 5) for connecting to lead assembly 60. The generator 10 is implanted in the patient's chest in a pocket or cavity formed by the implanting surgeon below the skin (indicated by a dotted line 90), similar to the implantation procedure for a pacemaker pulse generator. A stimulating nerve electrode assembly 70, preferably comprising an electrode pair 72, 74, is conductively connected to the distal end of an insulated electrically conductive lead assembly 60, which preferably comprises a pair of lead wires (one wire for each electrode of an electrode pair). Each lead wire in lead assembly 60 is attached at its proximal end to a connector 50 on case 27. The electrode assembly 70 is surgically coupled to a vagus nerve 100 in the patient's neck.

Figure 6:
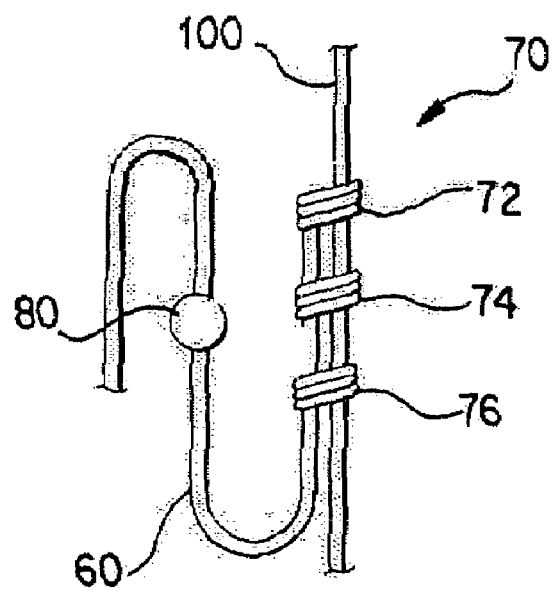
FIG. 6 shows a lead and electrodes suitable for use in the present invention attached to a vagus nerve of a patient.

The electrode assembly 70 preferably comprises a bipolar stimulating electrode pair (FIG. 6), such as the electrode pair described in U.S. Pat. No. 4,573,481 issued Mar. 4, 1986 to Bullara. Persons of skill in the art will appreciate that many electrode designs could be used in the present invention. The two electrodes are preferably wrapped about the vagus nerve 100, and the electrode assembly 70 is preferably secured to the nerve 100 by a spiral anchoring tether 76 (FIG. 6) such as that disclosed in U.S. Pat. No. 4,979,511 issued Dec. 25, 1990 to Reese S. Terry, Jr. and assigned to the same assignee as the instant application. Lead assembly 60 is secured, while retaining the ability to flex with movement of the chest and neck, by a suture connection 80 to nearby tissue.

In one embodiment, the open helical design of the electrode assembly 70 (described in detail in the above-cited Bullara patent), which is self-sizing and flexible, minimizes mechanical trauma to the nerve and allows body fluid interchange with the nerve. The electrode assembly 70 preferably conforms to the shape of the nerve, providing a low stimulation threshold by allowing a large stimulation contact area with the nerve. In one embodiment, the electrode assembly 70 comprises two electrode ribbons (not shown), of a conductive material such as platinum, iridium, platinum-iridium alloys, and/or oxides of the foregoing. The electrode ribbons preferably are individually bonded to an inside surface of an elastomeric body portion of the two spiral electrodes 72 and 74 (FIG. 6), which may comprise two spiral loops of a three-loop helical assembly.

The lead assembly 60 may comprise two distinct lead wires or a coaxial cable whose two conductive elements are respectively coupled to one of the conductive electrode ribbons 72 and 74. One suitable method of coupling the lead wires or cable to the electrodes comprises a spacer assembly such as that disclosed in U.S. Pat. No. 5,531,778, although other known coupling techniques may be used. The elastomeric body portion of each loop is preferably composed of silicone rubber, and the third loop 76 (which typically has no electrode) acts as the anchoring tether for the electrode assembly 70.

Figure 4:
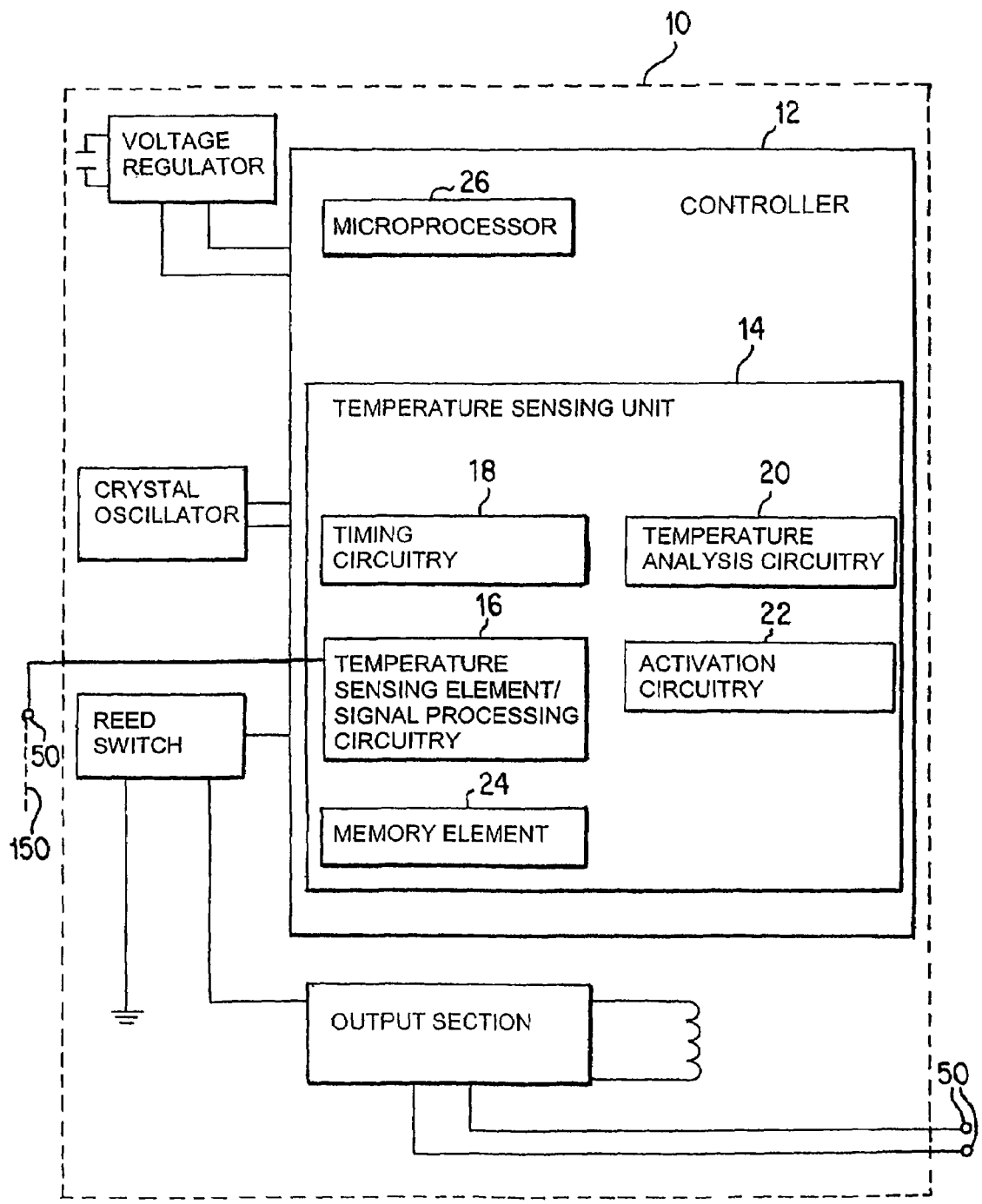
FIG. 4 is a block diagram of an implantable pulse generator in accordance with one illustrative embodiment of the present invention.

Referring to FIG. 4, distinct from the prior art, the pulse generator 10 of a preferred embodiment of the invention includes a controller 12 comprising a temperature sensing unit 14 for measuring the body temperature of a patient at predetermined or programmable intervals. The TSU 14 includes a temperature sensor element 16 such as a thermocouple, electrode, or a temperature sensor included as part of a microprocessor 26 or integrated circuit, timing circuitry 18 for controlling the rate at which temperature measurements are taken, and analysis circuitry 20 for calculating a number of temperature parameters such as time-weighted moving average temperatures and time rates of change of temperature. The TSU 14 may also include activation circuitry 22 for deciding when to trigger a stimulation burst from the pulse generator 10. Finally, a memory element 24 is used in conjunction with (or as part of) TSU 14 for storing measured and calculated temperature data.

It will be appreciated by persons of skill in the art that one or more of the components of TSU 14 as depicted in FIG. 4 may be depicted instead as other parts of the controller 12, or as other blocks within the stimulator 10, without lack of accuracy. For example, the timing circuitry and even the sensor element itself may be part of the microprocessor 26, and the element may comprise a RAM or other memory device known in the art. In addition, certain aspects of the invention may be implemented as hardware, firmware, software or combinations thereof. Persons of skill in the art will understand that circuit layout and hardware/firmware/software implementation decisions include numerous design choice issues, and unless specifically noted all such designs should be considered as falling within the scope and spirit of the invention.

Figure 2:
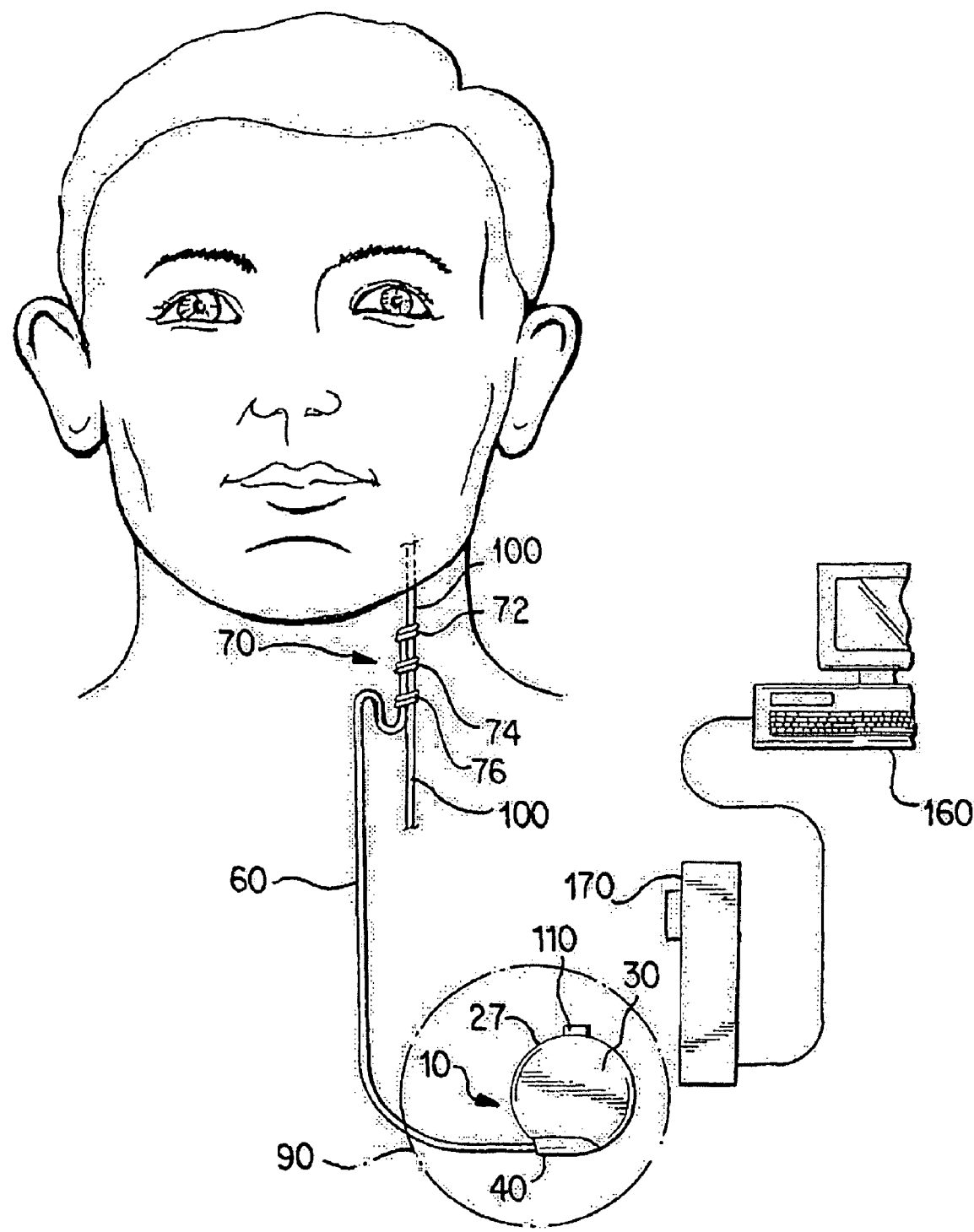
FIG. 2 is a stylized diagram of an embodiment of an implantable medical device suitable for use in the present invention, with a temperature sensor integrally coupled to a pulse generator case.

In certain embodiments of the invention, the temperature sensor element 16, such as sensor 110 (FIG. 2) may be provided integrally with case 27 for sensing temperature under the control of the timing circuitry 18. Pulse generator 10 is typically implanted in the patient's body with a first side facing the patient's skin and a second side facing the interior of the patient's body. Because the purpose of the sensor element 110 is to accurately measure the patient's core temperature, it is preferably located on the second side of pulse generator 10—facing the interior of the patient's body—to avoid temperature gradients induced from outside the patient's body.

Figure 3:
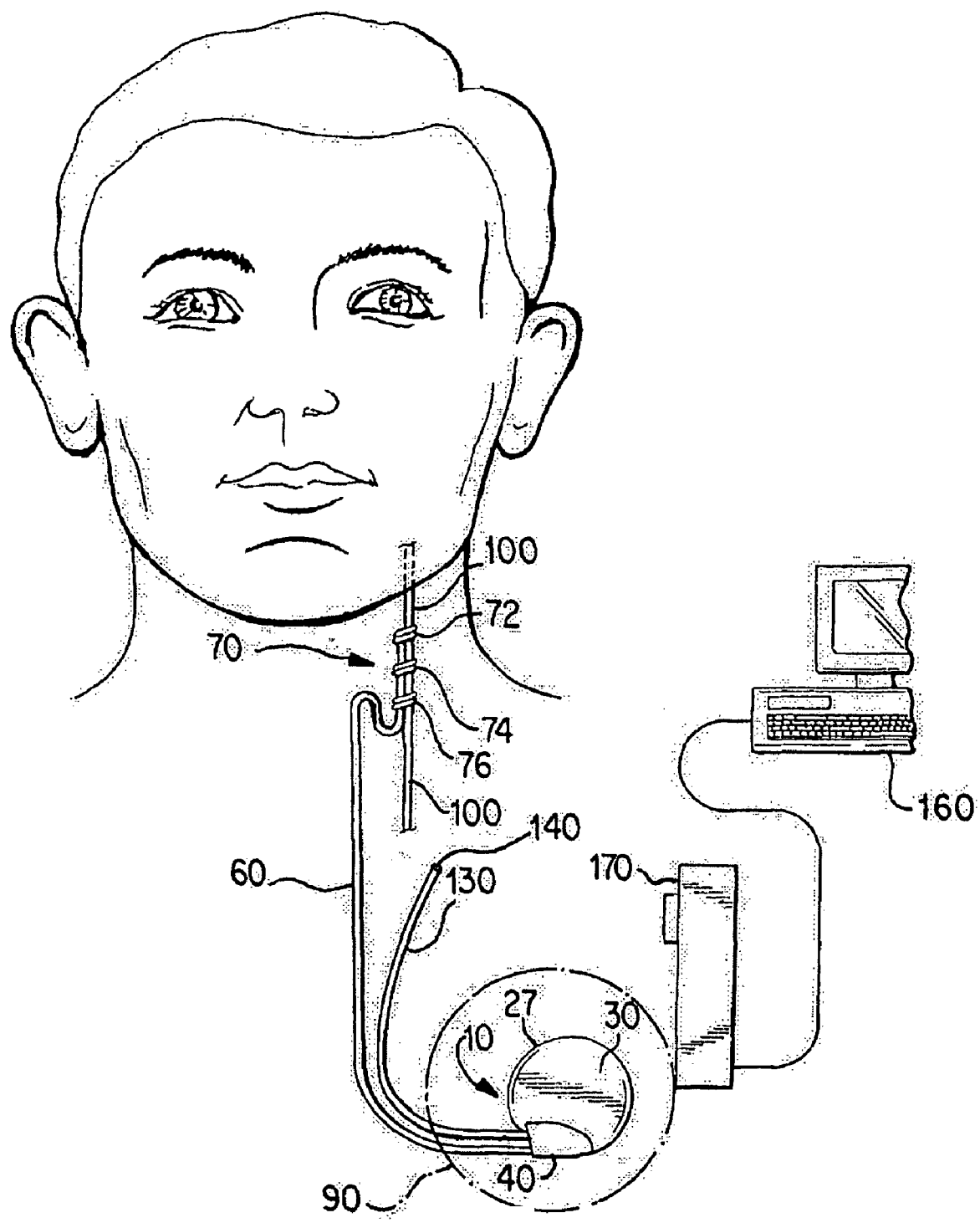
FIG. 3 is a stylized diagram of another embodiment of an implantable medical device suitable for use in the present invention, with a temperature sensor at the distal end of a lead coupled to a pulse generator.

In another embodiment, the temperature sensor element may comprise a thermocouple 140 at the distal end of a lead wire 130 coupled to a connector 50 on the pulse generator 10, as shown in FIG. 3. Alternatively, the thermocouple may be present at the distal end of a rigid member coupled to the pulse generator (not shown). In a further alternative embodiment, the thermocouple may be combined into lead assembly 60 (not shown). More generally, by placing the sensor element at the distal end of a conducting and spacing element, a more reliable indication of core body temperature may be obtained by locating the sensor element deeper insider the patient's body, thereby minimizing or removing altogether temperature effects from the exterior environment. In yet another alternative embodiment, the temperature data may be communicated to controller 12 via a data link (e.g., a radio frequency transmitter) from a temperature sensor physically disconnected from generator 10.

In a preferred embodiment, the temperature sensor element 16 comprises a silicon-based sensor element, preferably included as part of a microprocessor 26 or ASIC chip. Such a sensor element reduces the number of system components and consequently avoids failure modes, such as fatigue-induced failure of a lead wire, associated with sensor elements spaced remotely from the pulse generator 10. In addition, by including the sensor element as part of an integrated circuit chip within the pulse generator case 27, the sensor element 16 is protected from the harsh environment of the patient's body, contributing to potentially longer life of the sensor element 16 and avoiding premature failure. Moreover, one or more of the other elements of the temperature sensing unit 14, i.e., the timing circuitry 18, the analysis circuitry 20, activation circuitry 22, and memory element 24, may also be included as part of the same microprocessor 26 or ASIC chip.

Figure 5:
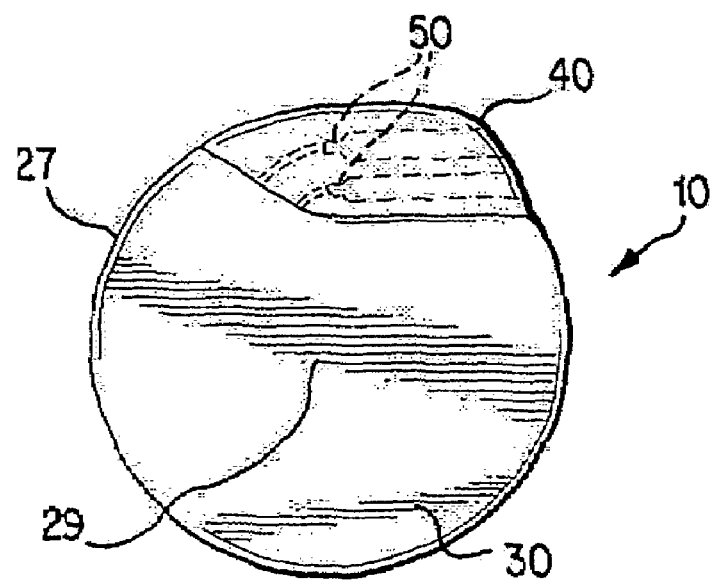
FIG. 5 illustrates an implantable pulse generator suitable for use in the present invention, showing the header and electrical connectors for coupling the device to a lead/electrode assembly.

A view of the first side 29 (i.e., the side facing the skin of the patient) of an implantable pulse generator 10 according to certain embodiments of the invention is illustrated in FIG. 5. The generator 10 comprises a header 40 equipped with at least two connector sockets for coupling an electrode assembly 70 and a temperature sensing element 16 to connectors 50 on the pulse generator. In the embodiment of FIG. 5, the electrode assembly 70 is coupled to a coaxial-type cable lead 60 that is connected to single connector socket having two connectors 50. A second connector socket is provided for connecting the proximal end of a second coaxial lead 130 to a pair of connectors 50, with the distal end of lead 130 being coupled in turn to a thermocouple 140 or other temperature probe, as shown in FIG. 3. In other embodiments, the temperature sensor element 16 is provided as part of a microprocessor 26 or ASIC chip located inside case 27 of pulse generator 10, and one or two connector sockets are provided in header 40 solely for connection to stimulation leads 60 (either a single coaxial socket or dual single-wire sockets). In another embodiment (not shown), the thermocouple 140 is provided as part of lead assembly 60, and one or two connector sockets are provided in header 40 for connecting the combined stimulation leads and thermocouple leads.

In fully implantable embodiments, the invention provides active stimulation by sensing temperature parameters that may be associated with an undesired physiological event, such as an epileptic seizure, and automatically initiating or adjusting cranial nerve stimulation therapy in response. In preferred embodiments, the TSU 14 is able to specifically detect temperature parameters outside of the patient's normal physiologic temperature parameters, and automatically initiate therapy when it is determined that a change in the temperature parameter is likely to be associated with an undesired physiological event. The parameters may comprise body temperature, rate of change of temperature, and moving average temperature differences, duration at an elevated or reduced temperature, and/or stability or instability of temperature over time.

Referring again to FIG. 4, in a particular embodiment of the neurostimulation system, a temperature sensor element 16 provides a time series data stream of body temperature measurement signals 150. The sampling rate of the time series data stream is controlled by timing circuitry 18, which preferably comprises registers allowing the sampling rate to be programmed by a user with external programming computer 160 and handheld programming wand 170. The data is preferably converted from analog to digital data by conventional digital-to-analog circuitry (not shown) and stored in memory element 24 for use by analysis circuitry 20. Alternatively, the temperate signal data stream may first be processed by analysis circuitry 20 (which in the alternative embodiment preferably comprises temporary memory storage capacity) and used to calculate one or more temperature parameters. The digital data, including both the temperature measurements and the calculated parameters, such as moving average temperatures and rates of change of temperature, are then stored in memory element 24.

The timing circuitry 18 preferably allows the temperature sampling rate to be programmed over a wide range of sampling rates, including rates ranging from more than 100 temperature measurements per second to less than 1 temperature measurement per hour. Although more precise indications of the occurrence of an undesired physiological event may be obtained at higher sampling rates, higher sampling rates require much higher power consumption and consequently significantly reduce battery life for a fully implantable system. Accordingly, sampling rates on the order of 1 second to 1 hour are most preferred. Extremely low sampling rates, such as one measurement each 30 minutes or hour, do not provide enough data to allow rapid temperatures to be detected, and thus are less preferred.

Timing circuitry 18 may also comprise sampling rate adjustment circuitry and/or logic (not shown) capable of changing the body temperature sampling rate based on, e.g., detected temperature changes, time of day, circadian rhythms, heart rate parameters, blood parameters, or other physiological, environmental, or temporal conditions.

Temperature analysis circuitry 20 provides a desirable feature of the present invention. In particular, the circuitry determines one or more temperature parameters and compares those parameters to threshold values. If a parameter exceeds its threshold value, which indicates that an undesired physiological event may have occurred or may soon occur, the circuitry causes activation circuitry 22 to generate stimulation signals for delivery to electrodes 72, 74 for stimulation of a cranial nerve.

In one embodiment, the temperature analysis circuitry 20 maintains a log of all temperature measurements for a predetermined log period, such as 24 hours, and also calculates and stores minimum and maximum temperatures, running average temperatures, rates of change of temperature, duration at an elevated or reduced temperature, and/or stability or instability of temperature over time for several shorter time domains within the log period. As a nonlimiting example, for a system in which timing circuitry 18 provides a one minute sampling rate, analysis circuitry 20 may maintain a log of stored body temperature readings for the previous 1 hour, and may calculate and store rates of temperature change for the previous two minute, three minute and five minute periods based on the temperature readings for the most recent five minute period. If the temperature change for the previous two minute period exceeds 1° F., or the previous five minute change exceeds 1.5° F., the activation circuitry may initiate stimulation of a vagus nerve of the patient. In addition, the analysis circuitry 20 may calculate a two minute, five minute, and ten minute running average body temperature reading for the most recent ten minute period. If the moving average temperature for the previous two minute period differs from that of either the five or ten minute moving average temperatures by more than 0.5° F., the activation circuitry may likewise initiate stimulation of a vagus nerve of the patient. It is understood that the time domains and temperature changes provided in the previous examples are exemplary only, and other time domains and temperature changes are within the scope of the invention.

In certain embodiments of the invention, maximum physiological temperature changes, rates of temperature change, changes between moving average temperatures, duration at an elevated or reduced temperature, and/or stability or instability of temperature over time may be determined empirically for a patient by exercise tests after the neurostimulation system has been implanted in the body of the patient. For example, the patient may perform various exercise tasks, and the effects of the exercise tasks on the foregoing temperature parameters noted and stored by the temperature sensing unit 14. If, for example, the patient's temperature rises by 2.0° F. over a five minute period, a rate of temperature change exceeding 0.4° F./minute can be used as a threshold above which any rate change will trigger or alter (e.g., by extending the duration of) a neurostimulation therapy. Whether determined empirically or otherwise, temperature parameter thresholds are preferably set at a rate that exceeds the rate of temperature change during periods of intense exercise and rates associated with extreme environmental temperature differences.

Using a plurality of temperature parameter changes in excess of a threshold level, rather than a single temperature parameter can reduce false positive detections. For example, TSU 14 can be programmed such that the analysis circuitry 20 will only initiate stimulation if two temperature parameters exceed a threshold level. In a specific example, the analysis circuitry 22 could require that the current temperature exceed 100° F. and that the rate of temperature change for the most recent five minutes exceed 0.5° F./minute before generating a therapy initiation signal and transmitting it to the activation circuitry 22. In a different embodiment, the analysis circuitry may require that the rate of temperature change for the preceding three minute interval exceed 0.2° F./minute and that the moving average temperature for the preceding two minutes exceed the moving average for the preceding 10 minutes by 1.0° F. before therapy is initiated.

The use of two or more temperature parameters to trigger therapy must be balanced against the fact that failure to detect an imminent undesired physiological event such as an epileptic seizure results in a missed opportunity to abort the seizure. In general, the failure to abort a seizure is a worse therapeutic outcome than neural stimulation in response to false positives, because the latter is not likely to produce harmful side effects.

On the other hand, an overly high sensitivity can result in continuous or nearly continuous therapy, which is not desirable. Preferably, the time interval between consecutive applications of nerve stimuli should be programmed and safeguards maintained to assure that a suitable minimum off time is provided to prevent overstimulation of a neural structure.

Although a preferred embodiment and method have been described herein, it will be apparent to persons skilled in the art of the invention, from a consideration of the foregoing disclosure, that variations and modifications of the disclosed embodiment and method may be made without departing from the spirit and scope of the invention. Accordingly, it is intended that the invention shall be limited only to the extent required by the appended claims and the rules and principles of applicable law.

What is claimed:

1. A method of providing electrical neurostimulation therapy to a cranial nerve of a patient comprising:
   generating a time series of temperature data representative of a body temperature of the patient;
   determining from said data at least two body temperature parameters for the patient over at least one predetermined time period, wherein said at least two body temperature parameters include first and second body temperature parameters;
   comparing the at least two body temperature parameters with respective thresholds, wherein said respective thresholds include first and second thresholds; and
   providing an electrical signal directly to a cranial nerve of the patient contingent upon:
   (i.) said first body temperature parameter exceeding the first threshold; and
   (ii.) said second body temperature parameter exceeding the second threshold.

2. The method of claim 1 wherein said at least two body temperature parameters are selected from the group consisting of a time rate of change of temperature over the first predetermined time period, a moving average temperature over the first predetermined time period, a rise in body temperature exceeding a first magnitude over the first predetermined time period, a drop in body temperature exceeding a first magnitude over the first predetermined time period, a body temperature exceeding a first target temperature for the first predetermined time period, a body temperature below a first target temperature for first predetermined time period, a minimum rate of change of body temperature during the first predetermined time period, a maximum rate of change of body temperature during the first predetermined time period, and a temperature stability parameter for the first predetermined time period.

3. The method of claim 2 wherein said temperature stability parameter comprises a duration that body temperature is within a first temperature range, a duration that body temperature is outside a first temperature range, a difference between minimum and maximum body temperatures measured during the first predetermined time period, a standard deviation of body temperature measurements taken over the first predetermined time period, a difference between the minimum and maximum rates of change of body temperature during the first predetermined time period, and standard deviation of rates of change of body temperature during the first predetermined time period.

4. The method of claim 1, wherein providing an electrical signal directly to a cranial nerve comprises providing an electrical signal to a vagus nerve, a trigeminal nerve, or a glossopharyngeal nerve.

5. The method of claim 1 wherein said step of providing the electrical signal comprises performing an action selected from the group consisting of:
   applying the electrical signal directly to said cranial nerve in response to determining that the at least two body temperature parameters exceed the respective first and second thresholds, and
   changing an electrical parameter of said electrical signal directly applied to said cranial nerve in response to determining that the at least two body temperature parameter parameters exceed the respective first and second thresholds,
   wherein said electrical parameter is selected from the group consisting of current amplitude, a pulse width, a frequency, a pulse period, a cycle on-time and a cycle off-time.

6. The method of claim 5 wherein changing an electrical parameter comprises changing the electrical parameter in proportion to a change in said at least two body temperature parameters.

7. The method of claim 1 wherein generating a time series of temperature data comprises sensing body temperature of the patient with a temperature sensor, said time series of temperature data having a sampling interval that may be changed by programming the sampling interval and determining that at least said first body temperature parameter exceeds the first threshold.

8. The method of claim 1 further comprising storing said time series temperature data in a memory.

9. The method of claim 1 wherein said at least one predetermined time period comprises a plurality of predetermined time periods.

10. The method of claim 1 wherein said at least one predetermined time period comprises a time period within the group of time periods ranging from 0.01 seconds to 24 hours.

11. The method of claim 1 wherein said first threshold comprises a threshold associated with physical exercise by the patient.

12. The method of claim 11 further comprising testing the patient with an exercise test to determine said first threshold associated with physical exercise.

13. The method of claim 12 wherein said first threshold associated with physical exercise comprises a maximum body temperature achieved during exercise, a maximum rate of increase of body temperature over a predetermined exercise time period, and a time period during which the body temperature exceeds a predetermined target temperature.

14. The method of claim 1 wherein providing said electrical signal directly to said cranial nerve of the patient includes repeatedly applying electrical neurostimulation therapy with a predetermined off time interval between consecutive applications.

15. The method of claim 1 wherein generating a time series of temperature data comprises sensing body temperature of the patient with a temperature sensor, said time series of temperature data having a sampling interval that is adjustable by programming the sampling interval based on at least one of: time of day, a circadian rhythm of the patient, a heart rate parameter of the patient and a blood parameter of the patient.

* * * * *